United States Patent
Retsina et al.

(10) Patent No.: US 9,145,529 B2
(45) Date of Patent: *Sep. 29, 2015

(54) PROCESSES FOR PRODUCING ENERGY-DENSE BIOMASS FOR COMBUSTION

(71) Applicant: API Intellectual Property Holdings, LLC, Atlanta, GA (US)

(72) Inventors: Theodora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/173,332

(22) Filed: Feb. 5, 2014

(65) Prior Publication Data

US 2014/0150334 A1 Jun. 5, 2014

Related U.S. Application Data

(63) Continuation of application No. 13/829,355, filed on Mar. 14, 2013, now Pat. No. 8,906,657.

(60) Provisional application No. 61/612,453, filed on Mar. 19, 2012.

(51) Int. Cl.
| | |
|---|---|
| *C12P 7/10* | (2006.01) |
| *C10L 5/44* | (2006.01) |
| *C13K 13/00* | (2006.01) |
| *F23G 7/10* | (2006.01) |
| *C12P 19/02* | (2006.01) |
| *C12P 19/14* | (2006.01) |

(52) U.S. Cl.
CPC . *C10L 5/44* (2013.01); *C12P 19/02* (2013.01); *C12P 19/14* (2013.01); *C13K 13/007* (2013.01); *F23G 7/10* (2013.01); *F23G 7/105* (2013.01); *F23G 2900/50206* (2013.01); *Y02E 50/10* (2013.01); *Y02E 50/15* (2013.01); *Y02E 50/16* (2013.01); *Y02E 50/30* (2013.01)

(58) Field of Classification Search
USPC .......................................... 435/165; 127/37
See application file for complete search history.

(56) References Cited

U.S. PATENT DOCUMENTS

| | | | |
|---|---|---|---|
| 8,497,105 B2 * | 7/2013 | Walther et al. ................ 435/160 |
| 2010/0330633 A1 * | 12/2010 | Walther et al. ................ 435/150 |
| 2012/0009632 A1 | 1/2012 | Retsina et al. | |

FOREIGN PATENT DOCUMENTS

WO 2011020082 A1 2/2011

OTHER PUBLICATIONS

International Preliminary Report on Patentability for PCT/US2013/032022, received Oct. 2, 2014.
Zhu and Pan, "Woody biomass pretreatment for cellulosic ethanol production: Technology and energy consumption evaluation," Bioresource Technology 101 (2010) 4992-5002.

* cited by examiner

*Primary Examiner* — Ralph Gitomer
(74) *Attorney, Agent, or Firm* — Ryan P. O'Connor

(57) ABSTRACT

This invention provides processes to convert biomass into energy-dense biomass for combustion, alone or in combination with another solid fuel. Some embodiments provide processes for producing energy-dense biomass from cellulosic biomass, comprising extracting the feedstock with steam and/or hot water to produce an extract liquor containing hemicellulosic oligomers, dissolved lignin, and cellulose-rich solids; separating the extract liquor, to produce dewatered cellulose-rich solids; hydrolyzing the dewatered cellulose-rich solids, thereby removing a portion of the cellulose, to produce intermediate solids (with higher energy density) and a hydrolysate; drying the intermediate solids to produce energy-dense biomass; and optionally recovering fermentable sugars from the hydrolysate. The energy-dense biomass may be pelletized into biomass pellets, which may have a similar energy density as torrefied pellets from wood. The hemicellulosic oligomers may be further hydrolyzed to produce additional fermentable sugars. The fermentable sugars may be fermented to ethanol or another product.

20 Claims, 2 Drawing Sheets

PROCESSES FOR PRODUCING ENERGY-DENSE BIOMASS FOR COMBUSTION

PRIORITY DATA

This patent application is a continuation patent application of U.S. Pat. No. 8,906,657, issued on Dec. 9, 2014, which claims priority to U.S. Provisional Patent App. No. 61/612,453, filed Mar. 19, 2012, each of which is hereby incorporated by reference herein.

STATEMENT REGARDING FEDERALLY SPONSORED RESEARCH OR DEVELOPMENT

This invention was made with Government support under Contract No. DE-EE0002868. The Government has certain rights in this invention.

FIELD OF THE INVENTION

The present invention generally relates to processes for preparing energy-dense biomass for combustion, while also recovering fermentable sugars from the starting biomass.

BACKGROUND OF THE INVENTION

Wood and biomass burning is making a comeback after over a century of domination by coal, petroleum, and natural gas for power generation. The availability of energy-dense fossil fuels and efficient transportation networks made centralized power production the technology of choice. In the 21st century, biomass heat and power plants and district heating are enjoying a renaissance. This popularity is driven in part by the carbon-neutral nature of most biomass (i.e., no net $CO_2$ emissions). The rising cost of fossil fuels and incentives for switching drive consumer decisions toward renewable energy. Also, renewable-energy portfolio mandates require that utilities construct renewable power plants.

One challenge to combusting biomass is its high moisture content. Living and freshly cut biomass typically contains moisture between 40% and 60%. In loose storage, the biomass dryness can reach air-dry moisture of about 10%. This drying of wood is slow, typically requiring at least a full summer season. This necessitates double handling and increases procurement cost. It can be advantageous to first pelletize biomass, which can drive moisture out of the biomass, by using part of the biomass energy, waste heat, or a fossil fuel. The final moisture from pelletizing is typically 5-7%, which is similar to moisture of coal. Boiler efficiencies increase approximately half a percent with each percentage removal of moisture.

In biomass, cellulose and hemicellulose each have about half of the calorific heat value of coal, because of high oxygen content of polymeric sugar constituents. Lignin has a similar calorific heat value to coal, but sulfur is nearly absent. The combined energy content of biomass is typically 8,000-9,000 Btu/lb, as compared to 10,000-14,000 Btu/lb in coal. Because of high oxygen content and moisture in biomass, the boiler efficiency for biomass firing typically ranges from 50-65%. A large portion of heat generated in combustion escapes as steam through the stack. Therefore, converting coal-burning boilers to biomass firing may reduce boiler capacity by as much as 60%. There is a need to maximize utilization of these assets, and therefore more energy-dense biomass is desired.

Feeding irregularly shaped biomass also represents a challenge. Pelletizing can produce uniformly sized material that does not bridge or lodge easily in a storage silo. On the other hand, the pelletized material can absorb moisture, if stored loosely outdoors.

Another obstacle is presented by the ash in the biomass. Ash content of biomass typically varies between 0.4% and 15%. Hardwood and softwood stem and forest trimmings contain only 0.4% to 0.8% ash that is rich in calcium and potassium. Other biomass materials including pulp and paper sludge, paper waste, recycled paper and construction waste, can contain up to 30% ash. Such ash includes minerals in plant capillaries, dirt on the surface, and coating in the paper. The wood exposed to salt water contains elevated levels of sodium and chlorides.

Agricultural residues of annual plants, such as corn stover, corn fiber, wheat straw, sugarcane bagasse, rice straw, oat straw, barley straw, and miscanthus can contain up to 10% or more ash that is rich in silica, potassium, and chlorine. The agricultural residue material is very lean in sulfur, typically less than 0.1%, versus coal sulfur content of 0.5-7.5%. Significant minerals in these annual agricultural residues include potassium, sodium, silica, calcium, and corrosive halogens such as chlorides.

Upon combustion at high temperatures, metals and halogens volatilize to aerosols and carry over from the boiler with flue gas. The cooling of fly ash creates microscopic particles that are found to cause respiratory illnesses. Flue-gas treatment for particulate removal includes cyclones, scrubbers, and electrostatic precipitators (ESP). These environmental controls in the central power plant are expensive and, in domestic applications, tend to be cost-prohibitive. Recent Maximum Achievable Control Technology (MACT) legislation by the U.S. EPA seeks to control particulate emissions from large biomass power plants. Other minerals such as calcium and silica remain in the bottom of the boiler and have tendency to form clinkers and to scale (slag) in the boiler tubes. Alkaline chloride salts can cause corrosion of the boiler tubes.

What are needed are processes and apparatus to prepare biomass, including wood and agricultural residues, into clean, energy-dense biomass for improved combustion, with or without first pelletizing the biomass. The energy-dense biomass should be capable of being fired alone or in combination with another solid fuel. It would be desirable for these processes to also have good potential to recover various co-products, such as fermentable sugars, fertilizers, and lignin.

SUMMARY OF THE INVENTION

The present invention addresses the aforementioned needs in the art.

In some variations, the invention provides a process for producing energy-dense biomass and fermentable sugars from cellulosic biomass, the process comprising:

(a) providing a feedstock comprising cellulosic biomass;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass; and (f) optionally recovering fermentable sugars from the hydrolysate.

In some embodiments, the extraction solution comprises steam in saturated, superheated, or supersaturated form. In some embodiments, the extraction solution comprises hot water. The extraction solution may further sulfur dioxide, sulfurous acid, sulfuric acid, or any combination thereof. In some embodiments, the extraction solution contains from about 0.01 wt % to about 10 wt % acetic acid.

In some embodiments, step (c) includes washing the cellulose-rich solids using an aqueous wash solution, to produce a wash filtrate; and optionally combining at least some of the wash filtrate with the extract liquor. Step (c) may also include pressing the cellulose-rich solids to produce dewatered cellulose-rich solids and a press filtrate; and optionally combining at least some of the press filtrate with the extract liquor.

Prior to step (d), the dewatered cellulose-rich solids may be refined or milled. In some embodiments, step (d) employs cellulase enzymes for hydrolyzing the dewatered cellulose-rich solids. The enzymes may be recycled.

In some embodiments, step (d) employs a dilute acid for hydrolyzing the dewatered cellulose-rich solids. Step (d) may employ a weak acid for hydrolysis, such as acetic acid.

The hydrolysis in step (d) may be integrated with the separation in step (c). For example, hydrolyzing the dewatered cellulose-rich solids may be integrated with the washing, or may follow washing of the dewatered cellulose-rich solids. In some embodiments, hydrolyzing the dewatered cellulose-rich solids is initiated prior to pressing, or following pressing. Steps (c) and (d) may be conducted in a single unit or in different units.

Removal of cellulose in step (d) increases the energy content of the remaining solids to form the energy-dense biomass. The process of the invention may further include combusting the energy-dense biomass to produce power and/or heat, at the same location or a different location.

In some embodiments, the process comprises pelletizing the intermediate solids, to produce biomass pellets. The biomass pellets may have a similar energy density as torrefied pellets from wood, for example. In some embodiments, the biomass pellets have an energy content from about 8,500 Btu/lb to about 12,000 Btu/lb on a dry basis, such as about 9,000 Btu/lb, 10,000 Btu/lb, or higher on a dry basis.

The process may further include hydrolyzing the hemicellulosic oligomers contained in the extract liquor, under effective hydrolysis conditions, to produce fermentable hemicellulosic sugars; and then recovering the fermentable hemicellulosic sugars. The fermentable hemicellulosic sugars may be combined with the fermentable sugars derived from step (f), to form a combined biomass-sugars stream. Alternatively, the fermentable hemicellulosic sugars may be separately recovered from the fermentable sugars derived from step (f), for separate processing or use.

In some embodiments, the process further comprises removing a vapor stream comprising water and vaporized acetic acid from the extract liquor in at least one evaporation stage at a pH of 4.8 or less, to produce a concentrated extract liquor comprising the fermentable hemicellulosic sugars.

The process may further comprise removing at least a portion of the dissolved lignin from the extract liquor, to generate recovered lignin. The recovered lignin can be co-combusted with the intermediate solids. In some embodiments, the process includes binding the dewatered cellulose-rich solids with a binder comprising the recovered lignin, to produce the biomass pellets.

In some embodiments, the process further comprises a step of fermenting the fermentable hemicellulosic sugars to a fermentation product, such as ethanol, 1-butanol, or isobutanol.

Some variations of the invention provide a process for producing biomass pellets and fermentable sugars from cellulosic biomass, the process comprising:

(a) providing a feedstock comprising cellulosic biomass;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass;

(f) pelletizing the energy-dense biomass to form the biomass pellets; and (g) optionally recovering fermentable sugars from the hydrolysate.

The biomass pellets may have an energy content from about 8,500 Btu/lb to about 12,000 Btu/lb on a dry basis. In some embodiments, the biomass pellets have an energy content of at least 9,000 Btu/lb or at least 10,000 Btu/lb on a dry basis.

Certain variations of the invention provide a process for producing biomass pellets and fermentable sugars from cellulosic biomass, the process comprising:

(a) providing a feedstock comprising cellulosic biomass;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass;

(f) pelletizing the energy-dense biomass to form the biomass pellets;

(g) optionally recovering fermentable sugars from the hydrolysate; and (h) optionally hydrolyzing the hemicellulosic oligomers contained in the extract liquor, under effective hydrolysis conditions, to produce hemicellulosic sugars.

Optionally, some or all of the hemicellulosic sugars are combined with the fermentable sugars derived from step (g), to form a combined biomass-sugars stream. In some embodiments, the hemicellulosic sugars are separately recovered from the fermentable sugars derived from step (g).

Some embodiments of the invention enable processing of agricultural residues, such as corn stover, corn fiber, wheat straw, sugarcane bagasse, rice straw, oat straw, barley straw, miscanthus, energy cane, or combinations thereof. In certain embodiments, sugarcane bagasse is converted into energy-dense biomass and fermentable sugars.

In some embodiments, a process for producing energy-dense biomass and fermentable sugars from an agricultural residue comprises:

(a) providing a feedstock comprising an agricultural residue;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass; and (f) optionally recovering fermentable sugars from the hydrolysate.

In some embodiments, a process for producing biomass pellets and fermentable sugars from an agricultural residue comprises:

(a) providing a feedstock comprising an agricultural residue;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass;

(f) pelletizing the energy-dense biomass to form the biomass pellets; and (g) optionally recovering fermentable sugars from the hydrolysate.

In some embodiments, a process for producing biomass pellets and fermentable sugars from an agricultural residue comprises:

(a) providing a feedstock comprising an agricultural residue;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass;

(f) pelletizing the energy-dense biomass to form the biomass pellets;

(g) optionally recovering fermentable sugars from the hydrolysate; and (h) optionally hydrolyzing the hemicellulosic oligomers contained in the extract liquor, under effective hydrolysis conditions, to produce hemicellulosic sugars.

DETAILED DESCRIPTION OF EMBODIMENTS OF THE INVENTION

Figure 1:
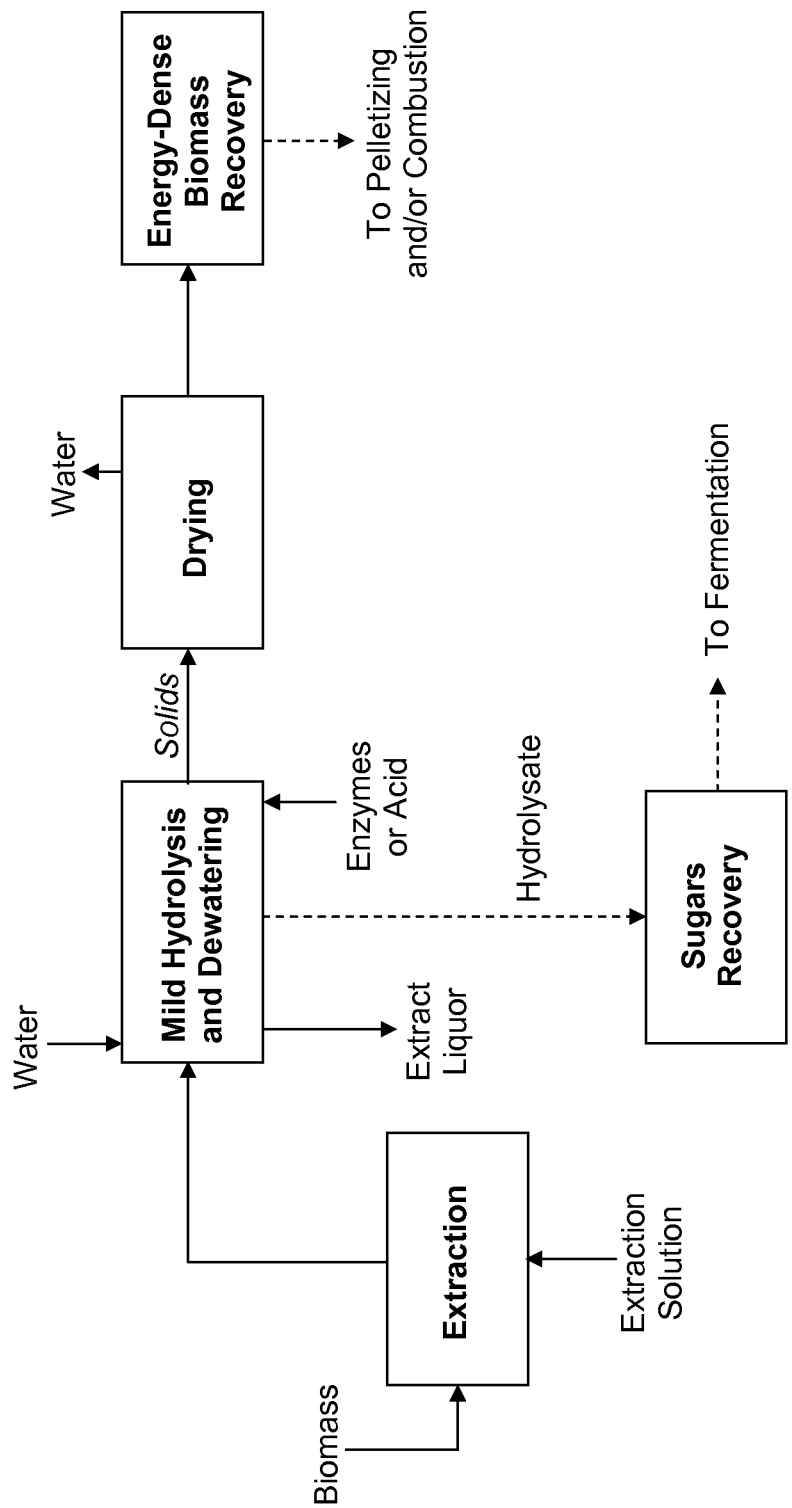
FIG. 1 is a simplified block-flow diagram depicting the process of some embodiments of the present invention, wherein energy-dense biomass is produced optionally with fermentable sugars derived from mild hydrolysis of cellulose-rich solids.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The present invention is premised, at least in part, on the realization that pretreatment of biomass may be utilized to remove hemicellulose and cellulose from the biomass, and thereby significantly increase the energy density of the biomass. The pretreated biomass will also be cleaned of ash components, to reduce particulate emissions upon combustion of the biomass. The extract may be further treated to make fermentable sugars, and optionally fermentation products. In an integrated process, unused solids or other combustible components recovered at any point may be co-combusted with the pretreated biomass, or separately recovered.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

The biomass feedstock may be selected from hardwoods, softwoods, forest residues, agricultural residues (such as sugarcane bagasse), industrial wastes, consumer wastes, or combinations thereof.

In some embodiments, such as the process depicted in FIG. 1, the process starts as biomass is received or reduced to approximately ¼" thickness. In a first step of the process, the biomass chips are fed to a pressurized extraction vessel operating continuously or in batch mode. The chips may be steamed or water-washed to remove dirt and entrained air. The chips are immersed with aqueous liquor or saturated vapor and heated to a temperature between about 100° C. to about 250° C., for example 150° C., 160° C., 170° C., 180° C., 190° C., 200° C., or 210° C. Preferably, the chips are heated to about 180° C. to 210° C. The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips. The vapor can be used for heating the incoming woodchips or cooking liquor, directly or indirectly. The volatilized organic acids (e.g., acetic acid), which are generated or included in the cooking step, may be recycled back to the cooking.

A third step may include washing the extracted chips. The washing may be accomplished with water, recycled condensates, recycled permeate, or combination thereof. A liquid biomass extract is produced. A countercurrent configuration may be used to maximize the biomass extract concentration. Washing typically removes most of the dissolved material, including hemicelluloses and minerals. The final consistency of the dewatered cellulose-rich solids may be increased to 30% or more, preferably to 50% or more, using a mechanical pressing device.

The third step, or an additional step prior to drying, may include further hydrolyzing the extracted chips with enzymes or an acid to extract some of the cellulose as fermentable glucose. The removal of cellulose increases the heating value of the remaining lignin-rich solids. In certain embodiments, the heating value of the remaining solids can approach that of lignin, i.e. in the range of about 10,000 to 12,000 Btu/lb. In some preferred embodiments, the additional hydrolysis is mild hydrolysis that leaves a substantial portion of cellulose in the extracted solids. The mild hydrolysis can take advantage of the initial extraction (first step) of most or all of the hemicellulosic material, leaving a somewhat hollow structure. The hollow structure can increase the effectiveness of cellulose hydrolysis, such as by reducing mass-transfer limitations of enzymes or acids in solution.

When enzymes are employed for the cellulose hydrolysis, the enzymes are preferably cellulase enzymes. Enzymes may be introduced to the extracted chips along with the wash solution, e.g. water, recycled condensates, recycled permeate, or combinations thereof. Alternatively, or additionally, enzymatic hydrolysis may be carried out following washing and removal of hemicelluloses, minerals, and other soluble material.

Enzymes may be added to the extracted chips before or after mechanical pressing. That is, enzymatic hydrolysis may be carried out and then the solids pressed to final consistency; or, the solids may be pressed to high consistency (e.g., 30% or more) and then enzymes introduced to carry out cellulose hydrolysis. It may be beneficial to conduct refining or milling of the dewatered cellulose-rich solids prior to the enzymatic hydrolysis.

The enzymatic hydrolysis may be achieved in a separate unit, such as between washing and drying, or as an integrated part of washing. In some embodiments, at least a portion of enzymes are recycled in a batch or continuous process.

When an acid is employed for the cellulose hydrolysis, the acid may be selected from sulfuric acid, sulfurous acid, sulfur dioxide, formic acid, acetic acid, oxalic acid, or combinations thereof. Dilute-acid hydrolysis is preferred, to avoid sugar degradation. Acids may be introduced to the extracted chips along with the wash solution, e.g. water, recycled condensates, recycled permeate, or combinations thereof. Alternatively, or additionally, acid hydrolysis may be carried out following washing and removal of hemicelluloses, minerals, and other soluble material.

Acids may be added to the extracted chips before or after mechanical pressing. That is, acid hydrolysis may be carried out and then the solids pressed to final consistency; or, the solids may be pressed to high consistency (e.g., 30% or more) and then acids introduced to carry out cellulose hydrolysis. It may be beneficial to conduct refining or milling of the dewatered cellulose-rich solids prior to the acid hydrolysis.

The acid hydrolysis may be achieved in a separate unit, such as between washing and drying, or as an integrated part of washing. In some embodiments, at least a portion of the acid is recycled in a batch or continuous process.

A fourth step may include drying of the extracted material to a desired final moisture. The heat necessary for drying may be derived from combusting part of the starting biomass. Alternatively, or additionally, the heat for drying may be provided by other means, such as a natural gas boiler or other auxiliary fossil fuel, or from a waste heat source.

A fifth step may include preparing the biomass for combustion. This step may include refining, milling, fluidizing, compacting, and/or pelletizing the dried, extracted biomass. The biomass may be fed to a boiler in the form of fine powder, loose fiber, pellets, briquettes, extrudates, or any other suitable form. In some embodiments, pellets of extracted biomass ("biomass pellets") are preferred. Using known equipment, biomass may be extruded through a pressurized chamber to form uniformly sized pellets or briquettes.

The energy-dense biomass will generally have higher energy density compared to a process that does not extract hemicellulosic sugars from the feedstock prior to combustion. Depleting the biomass of both hemicellulose and cellulose enriches the remaining material in lignin, which has a higher energy density than hemicellulose or cellulose.

In some embodiments, the energy density of the biomass pellet is similar to the energy density of a torrefied pellet derived from wood. For example, the biomass pellets may have an energy content from about 8,500 Btu/lb to about 12,000 Btu/lb on a dry basis, such as at least 9,000 Btu/lb or at least 10,000 Btu/lb on a dry basis.

A sixth step is combustion of the biomass, which in some embodiments is in the form of biomass pellets. The biomass pellets are fed to a boiler and combusted, preferably with excess air, using well-known combustion apparatus. Boiler bottom may be fixed, moving, or fluidized for the best efficiency. The flue gas is cooled and fly ash is collected into gravity collectors.

The energy-dense biomass has lower inorganic emissions potential compared to the original cellulosic biomass, in preferred embodiments. The reason is that the energy-dense biomass will contain lower ash content compared to a process that does not extract inorganic components from the feedstock prior to combustion, in the manner disclosed herein. In some embodiments, the extracted biomass is sufficiently low in ash such that when the extracted biomass is combusted, particulate matter emissions are very low. In certain embodiments, the particulate matter emissions are so low as to avoid the need for any additional cleaning device, and associated control system, in order to meet current emission regulations.

A seventh step may include treatment of the biomass extract to form a hydrolysate comprising fermentable hemicellulose sugars. In some embodiments, the biomass extract is hydrolyzed using dilute acidic conditions at temperatures between about 100° C. and 190° C., for example about 120° C., 130° C., 140° C., 150° C., 160° C., or 170° C., and preferably from 120° C. to 150° C.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis. Alternatively, hemicellulase enzymes may used instead of acid hydrolysis. The lignin from this step may be separated and recovered, or recycled to increase the heating value of the pellets, or sent directly to the boiler.

An eighth step may include evaporation of hydrolysate to remove some or most of the volatile acids. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. The dissolved solids are concentrated, such as to about 10% to about 40% to optimize fermentable hemicellulose sugar concentration to a particular microorganism. *Saccharomyces Cerevisiae* fermentation can withstand dissolved solids concentrations of 30-50%, while *Clostridia Acetobutylicum* fermentation is viable at 10-20% concentrations only, for example.

In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) and/or third step (washing step) to remove assist in the removal of minerals from the biomass. This recycle of organic acids, such as acetic acid, may be optimized along with process conditions that may vary depending on the amount recycled, to improve the cooking and/or washing effectiveness.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse.

Certain variations of the invention provide a process for producing biomass pellets and fermentable sugars from cellulosic biomass, the process comprising:

(a) providing a feedstock comprising cellulosic biomass;

(b) extracting the feedstock with steam and/or hot water under effective extraction conditions to produce an extract liquor containing hemicellulosic oligomers, dissolved lignin, and cellulose-rich solids;

(c) separating at least a portion of the cellulose-rich solids from the extract liquor, to produce dewatered cellulose-rich solids;

(d) hydrolyzing the dewatered cellulose-rich solids, thereby removing a portion of cellulose contained therein, to produce intermediate solids and a hydrolysate;

(e) drying the intermediate solids to produce the energy-dense biomass;

(f) pelletizing the energy-dense biomass to form biomass pellets;

(g) recovering fermentable sugars from the hydrolysate; and (h) hydrolyzing the hemicellulosic oligomers contained in the extract liquor, under effective hydrolysis conditions, to produce hemicellulosic sugars.

Figure 2:
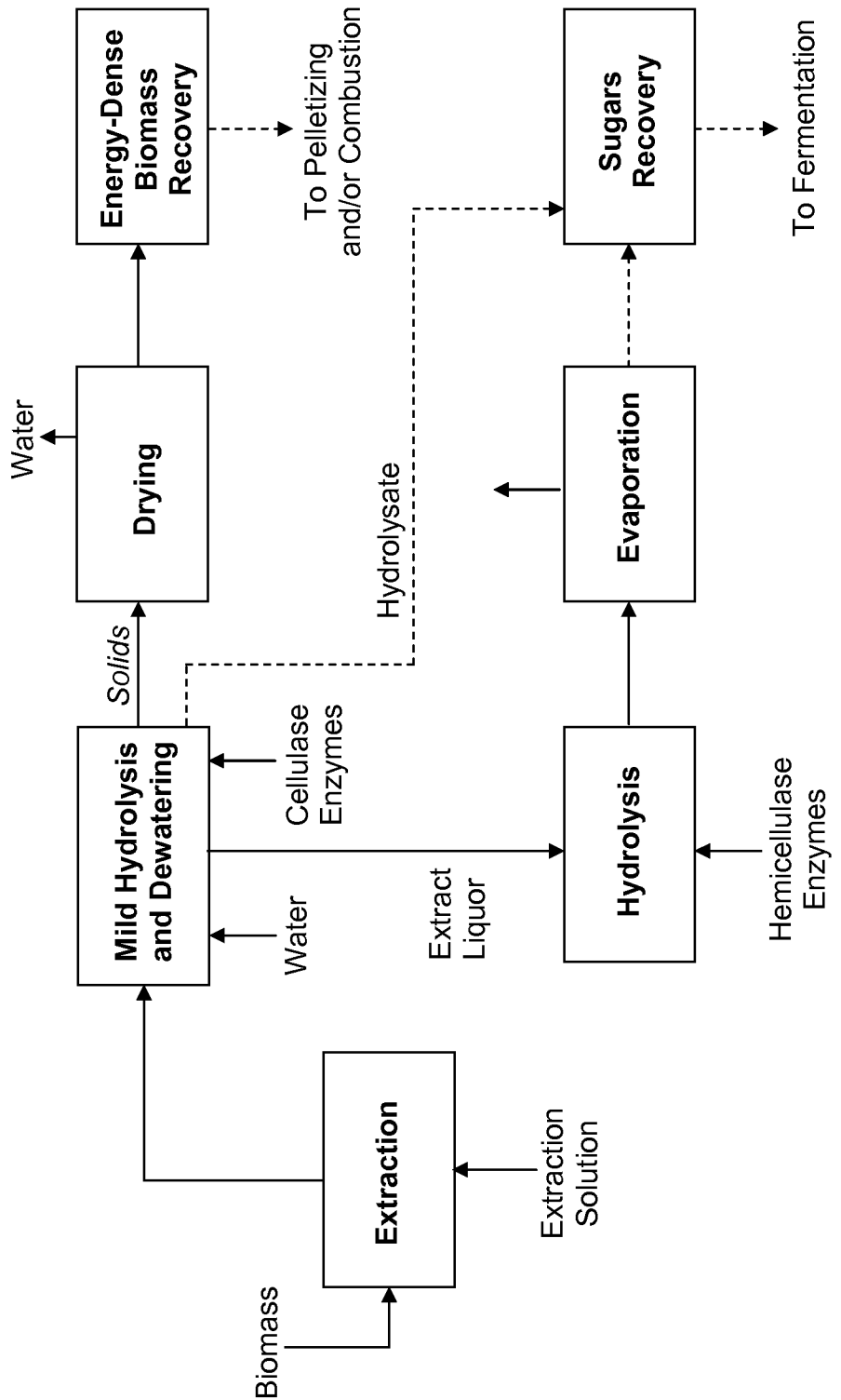
FIG. 2 is a simplified block-flow diagram depicting the process of certain embodiments of the present invention, wherein energy-dense biomass is produced optionally with fermentable sugars derived from both mild hydrolysis of cellulose-rich solids as well as optionally hydrolysis of hemicellulose oligomers released during initial extraction.

Optionally, some or all of the hemicellulosic sugars are combined with the fermentable sugars derived from step (g), to form a combined biomass-sugars stream (such as depicted in FIG. 2). In some embodiments, the hemicellulosic sugars are separately recovered from the fermentable sugars derived from step (g).

In some embodiments, the fermentable hemicellulose sugars are recovered from solution, in purified form. In some embodiments, the fermentable hemicellulose sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning as additional liquefied biomass, after concentration of the distillation bottoms.

Part or all of the residual solids may be co-combusted with the energy-dense biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

Optionally, the process may include co-combusting the recovered lignin with the energy-dense biomass, to produce power. The recovered lignin may be combined with the energy-dense biomass prior to combustion, or they may be co-fired as separate streams. When recovered lignin is combined with the energy-dense biomass for making pellets, the lignin can act as a pellet binder.

Part or all of the residual solids may be co-combusted with the energy-dense biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing energy-dense biomass and fermentable sugars from cellulosic biomass, said process comprising:
   (a) providing a feedstock comprising cellulosic biomass;
   (b) extracting said feedstock with steam and/or hot water under effective extraction conditions to produce an extract liquor containing each of hemicellulosic oligomers, lignin, and cellulose-rich solids, wherein said extracting is conducted with no added acid or with one or more added acids selected from the group consisting of sulfuric acid, sulfurous acid, sulfur dioxide, acetic acid, formic acid, or oxalic acid, and combinations thereof;
   (c) washing said cellulose-rich solids using an aqueous wash solution, to produce washed cellulose-rich solids and a hydrolysate;
   (d) separating said cellulose-rich solids from said hydrolysate;
   (e) mildly hydrolyzing said washed cellulose-rich solids with enzymes, thereby removing a portion of cellulose contained in said washed cellulose-rich solids, to generate intermediate solids;
   (f) drying said intermediate solids to produce energy-dense biomass; and
   (g) recovering fermentable sugars from said hydrolysate.

2. The process of claim 1, wherein step (b) includes extracting with said steam in saturated, superheated, or supersaturated form.

3. The process of claim 1, wherein step (b) includes extracting with said hot water.

4. The process of claim 1, said process further comprising combining at least some of a wash filtrate derived from said aqueous wash solution, with said extract liquor.

5. The process of claim 1, said process further comprising refining or milling said cellulose-rich solids or said intermediate solids.

6. The process of claim 1, wherein step (c) and step (d) are integrated.

7. The process of claim 1, wherein removal of cellulose in step (e) increases the energy content of said energy-dense biomass, compared to an otherwise-identical process that does not include step (e).

8. The process of claim 1, said process further comprising pelletizing said energy-dense biomass, to produce biomass pellets.

9. The process of claim 8, wherein said biomass pellets have an energy content from about 8,500 Btu/lb to about 12,000 Btu/lb on a dry basis.

10. The process of claim 9, wherein said biomass pellets have an energy content of at least 10,000 Btu/lb on a dry basis.

11. The process of claim 1, said process further comprising removing at least a portion of said lignin from said extract liquor, and adding said lignin to said intermediate solids.

12. The process of claim 1, said process further comprising combusting said energy-dense biomass to produce power and/or heat.

13. The process of claim 1, said process further comprising hydrolyzing said hemicellulosic oligomers contained in said extract liquor, under effective hydrolysis conditions, to produce fermentable hemicellulosic sugars; recovering said fermentable hemicellulosic sugars; and optionally combining said fermentable hemicellulosic sugars with said fermentable sugars derived from step (g).

14. The process of claim 1, said process further comprising a step of fermenting said fermentable sugars to a fermentation product.

15. A process for producing energy-dense biomass and fermentable sugars from cellulosic biomass, said process comprising:
   (a) providing a feedstock comprising cellulosic biomass;
   (b) extracting said feedstock with steam and/or hot water under effective extraction conditions to produce an extract liquor containing each of hemicellulosic oligomers, lignin, and cellulose-rich solids, wherein said extracting is conducted with no added acid or with one or more added acids selected from the group consisting of sulfuric acid, sulfurous acid, sulfur dioxide, acetic acid, formic acid, or oxalic acid, and combinations thereof;
   (c) mildly hydrolyzing said cellulose-rich solids with enzymes, thereby removing a portion of cellulose contained in said cellulose-rich solids, to generate intermediate solids;
   (d) washing said intermediate solids using an aqueous wash solution, to produce washed intermediate solids and a hydrolysate;
   (e) separating said washed intermediate solids from said hydrolysate;
   (f) drying said washed intermediate solids to produce energy-dense biomass; and
   (g) recovering fermentable sugars from said hydrolysate.

16. The process of claim 15, said process further comprising pelletizing said energy-dense biomass, to produce biomass pellets.

17. The process of claim 15, said process further comprising combusting said energy-dense biomass to produce power and/or heat.

18. A process for producing energy-dense biomass and fermentable sugars from cellulosic biomass, said process comprising:

(a) providing a feedstock comprising cellulosic biomass;

(b) extracting said feedstock with steam and/or hot water under effective extraction conditions to produce an extract liquor containing each of hemicellulosic oligomers, lignin, and cellulose-rich solids, wherein said extracting is conducted with no added acid or with one or more added acids selected from the group consisting of sulfuric acid, sulfurous acid, sulfur dioxide, acetic acid, formic acid, or oxalic acid, and combinations thereof;

(c) washing said cellulose-rich solids using an aqueous wash solution, to produce washed cellulose-rich solids and a hydrolysate;

(d) mildly hydrolyzing said washed cellulose-rich solids with enzymes, thereby removing a portion of cellulose contained in said washed cellulose-rich solids, to generate intermediate solids;

(e) separating said intermediate solids from said hydrolysate;

(f) drying said intermediate solids to produce energy-dense biomass; and (g) recovering fermentable sugars from said hydrolysate.

19. The process of claim 18, said process further comprising pelletizing said energy-dense biomass, to produce biomass pellets.

20. The process of claim 18, said process further comprising combusting said energy-dense biomass to produce power and/or heat.

* * * * *